US011594305B2

(12) United States Patent
Tregger et al.

(10) Patent No.: US 11,594,305 B2
(45) Date of Patent: Feb. 28, 2023

(54) MANAGING CONCRETE MIX DESIGN CATALOGS

(71) Applicant: VERIFI LLC, Cambridge, MA (US)

(72) Inventors: Nathan A. Tregger, Northborough, MA (US); Mark F. Roberts, North Andover, MA (US); Lawrence R. Roberts, Acton, MA (US); Gregory A. Goldstein, Arlington, VA (US)

(73) Assignee: VERIFI LLC, Cambridge, MA (US)

( * ) Notice: Subject to any disclaimer, the term of this patent is extended or adjusted under 35 U.S.C. 154(b) by 299 days.

(21) Appl. No.: 16/956,704

(22) PCT Filed: Dec. 11, 2018

(86) PCT No.: PCT/US2018/064822
§ 371 (c)(1),
(2) Date: Jun. 22, 2020

(87) PCT Pub. No.: WO2019/125813
PCT Pub. Date: Jun. 27, 2019

(65) Prior Publication Data
US 2020/0402619 A1 Dec. 24, 2020

Related U.S. Application Data

(60) Provisional application No. 62/609,421, filed on Dec. 22, 2017.

(51) Int. Cl.
*G16C 20/70* (2019.01)
*B28C 5/42* (2006.01)
(Continued)

(52) U.S. Cl.
CPC .............. *G16C 20/70* (2019.02); *B28C 5/422* (2013.01); *B28C 7/024* (2013.01); *B28C 7/026* (2013.01); *G06Q 50/08* (2013.01)

(58) Field of Classification Search
CPC ......... G16C 20/70; B28C 5/422; B28C 7/024; B28C 7/026; G06Q 50/08; G06Q 10/06; Y02P 90/82
See application file for complete search history.

(56) References Cited

U.S. PATENT DOCUMENTS

| | | | |
|---|---|---|---|
| 4,008,093 | A | 2/1977 | Kitsuda et al. |
| 5,527,387 | A | 6/1996 | Anderson et al. |

(Continued)

FOREIGN PATENT DOCUMENTS

| | | |
|---|---|---|
| DE | 4237543 | 5/1994 |
| DE | 4437970 | 5/1996 |

(Continued)

OTHER PUBLICATIONS

Thomas, Form PCT/ISA/210, International Search Report for PCT/US2018/064822, dated Dec. 12, 2019, 2 pages.

(Continued)

*Primary Examiner* — Charles Cooley
(74) *Attorney, Agent, or Firm* — Craig K. Leon

(57) ABSTRACT

Process and system for managing a mix design catalog of a concrete producer that involves collecting slump curve data obtained during in-transit monitoring of delivered concrete loads made from a plurality of various mix designs, wherein each mix design is identified by a different identification code (regardless of whether components are different), clustering slump curve data having same movement characteristics according to assigned strength value, and selecting a mix design to produce, to display, or both to produce and to display, from among the two or more slump data curves of individual mix designs within the same data curve cluster. The selection is based on same movement characteristic and assigned strength value, and at least one factor relative to cost, performance, physical aspect, quality, or other charac- (Continued)

teristic of the concrete mix or its components. Exemplary methods for generating new mix designs are also set forth.

18 Claims, 6 Drawing Sheets

(51) Int. Cl.
*B28C 7/02* (2006.01)
*G06Q 50/08* (2012.01)

(56) References Cited

U.S. PATENT DOCUMENTS

| | | | |
|---|---|---|---|
| 5,713,663 | A | 2/1998 | Zandberg et al. |
| 5,752,768 | A * | 5/1998 | Assh .................. B28C 5/422 366/60 |
| 5,895,116 | A | 4/1999 | Kreinheder et al. |
| 6,042,258 | A | 3/2000 | Hines et al. |
| 6,224,250 | B1 | 5/2001 | Kreinheder et al. |
| 6,227,039 | B1 | 5/2001 | Te'eni |
| 6,484,079 | B2 | 11/2002 | Buckelew et al. |
| 6,611,755 | B1 | 8/2003 | Coffee et al. |
| 7,384,180 | B2 | 6/2008 | Jarvinen et al. |
| 7,386,368 | B2 | 6/2008 | Andersen et al. |
| 7,503,227 | B2 | 3/2009 | Davis et al. |
| 7,972,436 | B2 | 7/2011 | Ou et al. |
| 8,020,431 | B2 * | 9/2011 | Cooley ................. B28C 5/4231 366/60 |
| 8,058,377 | B1 | 11/2011 | Goc-Maciejewska et al. |
| 8,118,473 | B2 | 2/2012 | Compton et al. |
| 8,311,678 | B2 * | 11/2012 | Koehler .................. G05D 24/02 700/285 |
| 8,491,717 | B2 * | 7/2013 | Koehler .................. C04B 28/02 106/713 |
| 8,727,604 | B2 | 5/2014 | Compton et al. |
| 8,746,954 | B2 | 6/2014 | Cooley et al. |
| 8,764,272 | B2 | 7/2014 | Hazrati et al. |
| 8,764,273 | B2 | 7/2014 | Koehler et al. |
| 8,818,561 | B2 * | 8/2014 | Koehler ............... G01N 33/383 700/265 |
| 8,858,061 | B2 | 10/2014 | Berman |
| 9,199,391 | B2 | 1/2015 | Beaupre et al. |
| 8,960,990 | B2 | 2/2015 | Koehler et al. |
| 8,989,905 | B2 | 3/2015 | Sostaric et al. |
| 9,466,203 | B2 | 10/2016 | Jordan et al. |
| 9,518,870 | B2 | 12/2016 | Verdino et al. |
| 9,533,429 | B2 * | 1/2017 | Phares .................. B28C 7/0422 |
| 9,550,312 | B2 * | 1/2017 | Roberts ................. B28C 7/0454 |
| 9,625,891 | B2 | 4/2017 | Berman |
| 9,789,629 | B2 * | 10/2017 | Koehler .................. G05D 21/02 |
| 9,952,246 | B2 | 4/2018 | Jordan et al. |
| 10,183,418 | B2 * | 1/2019 | Jordan .................. B28C 5/422 |
| 10,329,202 | B2 * | 6/2019 | Tregger ............... C04B 40/0032 |
| 10,363,684 | B2 * | 7/2019 | Roberts .................. B28C 5/422 |
| 11,312,039 | B1 * | 4/2022 | Chapdelaine ........... B28C 7/024 |
| 11,420,358 | B2 * | 8/2022 | Beaupre .................. B28C 7/024 |
| 2002/0010525 | A1 | 1/2002 | Radjy et al. |
| 2002/0015354 | A1 | 2/2002 | Buckelew |
| 2002/0048212 | A1 | 4/2002 | Hill et al. |
| 2006/0026636 | A1 | 2/2006 | Stark et al. |
| 2006/0039233 | A1 | 2/2006 | Farrington et al. |
| 2007/0192257 | A1 | 8/2007 | Amey et al. |
| 2007/0266905 | A1 | 11/2007 | Amey et al. |
| 2008/0027583 | A1 | 1/2008 | Andersen |
| 2008/0027584 | A1 | 1/2008 | Andersen |
| 2008/0316856 | A1 | 12/2008 | Cooley et al. |
| 2009/0037026 | A1 | 2/2009 | Sostaric et al. |
| 2009/0158960 | A1 | 6/2009 | Andersen et al. |
| 2009/0171595 | A1 | 7/2009 | Benegas |
| 2011/0004332 | A1 | 1/2011 | Andersen |
| 2012/0016523 | A1 | 1/2012 | Koehler et al. |
| 2013/0019235 | A1 | 8/2013 | Fernald et al. |
| 2014/0104972 | A1 | 4/2014 | Roberts et al. |
| 2014/0241104 | A1 | 8/2014 | Phares et al. |
| 2014/0297204 | A1 | 10/2014 | Biesak et al. |
| 2015/0082862 | A1 | 3/2015 | Loose et al. |
| 2015/0247833 | A1 | 9/2015 | Radjy |
| 2017/0028586 | A1 | 2/2017 | Jordan et al. |
| 2017/0080600 | A1 | 3/2017 | Dickerman et al. |
| 2022/0234249 | A1 * | 7/2022 | Papania-Davis ...... B28C 7/0418 |

FOREIGN PATENT DOCUMENTS

| | | |
|---|---|---|
| EP | 0126573 | 11/1984 |
| EP | 0901017 | 3/1999 |
| GB | 1182590 | 2/1970 |
| GB | 2144240 | 2/1985 |
| GB | 2392502 | 3/2004 |
| GB | 2426347 | 11/2006 |
| GB | 2432675 | 5/2007 |
| JP | 2001097749 | 4/2001 |
| WO | 2007060272 | 5/2007 |
| WO | 2009126138 | 10/2009 |
| WO | 2009144523 | 12/2009 |
| WO | 2010111204 | 9/2010 |
| WO | 2013059466 | 10/2011 |
| WO | 2016014932 | 1/2016 |
| WO | 2017099711 | 6/2017 |
| WO | 2019032820 | 2/2019 |

OTHER PUBLICATIONS

Thomas, Form PCT/ISA/237, Written Opinion of The International Search Authority for PCT/US2018/064822, dated Dec. 12, 2019, 8 pages.

Brazilian communication, with English translation, dated Sep. 15, 2022 in corresponding Brazilian patent application No. BR112020012749-3.

* cited by examiner

MANAGING CONCRETE MIX DESIGN CATALOGS

FIELD OF THE INVENTION

The invention relates to the field of hydratable cementitious materials, and more particularly managing the mix design catalog of a concrete producer, based on identifying clusters of slump curve data obtained during in-transit concrete delivery monitoring of individual concrete loads made from various mix designs, and sorting each curve cluster based on selection factors as desired by the concrete producer.

BACKGROUND OF THE INVENTION

Concrete producers, such as manufacturers of ready-mix or precast concrete, require different concrete mix designs to meet strength and slump targets for various customers and to address various applications (e.g., pavements, columns). Typically, the design of a concrete mix takes into consideration various factors including cement type, aggregate type and ratio, water-to-cement ratio (w/c), chemical admixture (s), air characteristics, placing methods, and numerous other factors.

The term "mix design catalog" as used herein refers to the collection or accumulation of various concrete mix designs of a given concrete producer. Concrete producers rapidly accumulate concrete mix designs in their catalogs over time.

In the construction industry, successful concrete producers will typically have an extended history in the business. During expansion of the customer base or the acquisition of production plants, for example, a concrete producer can rapidly increase its number of product offerings from tens to hundreds, and from hundreds to thousands and even to tens of thousands. The proportion of significantly different and useful mix designs can vary widely. That is to say, for many concrete producers, there could be a large number of duplicative mix designs, which means that a number of designs could effectively be discarded from the mix design catalog. As will be explained, however, house cleaning can be a heavy burden on the concrete producer and frequently does not happen in the concrete industry.

Concrete producers collect concrete mix designs over time for numerous reasons. Such reasons include, as an example, different construction applications that require different aggregates, different aggregate blends, or different mix ratios (e.g., coarse to fine aggregate), different amounts of water depending on aggregate packages (See e.g., ACI 211-65), and different admixture components (e.g., air entrainers, corrosion inhibitors, plasticizers, etc.).

Various concrete mix designs can also arise due to a large number of specific technical or performance considerations and customer requirements. For example, material sources and raw materials change over time. These include cements, pozzolans, aggregates, chemical admixtures, and other components. Substitution of components can involve new blending ratios. All of these considerations give rise to new mix designs.

A sales team or quality control department can generate new mix designs to satisfy individual customer requests. Putting new mix design codes on "new" mix designs might entail minor changes in the actual component mixture. This could result in negligible differences in terms of quality or performance between two different mix designs.

The present inventors believe that over time the mix design catalog grows in size because old mix designs are retained in the catalog even as new mix designs are added. As a new mix design often requires laboratory or full-scale testing to confirm performance, producers hesitate to remove mix designs from their catalogs. This is partly due to the desire to avoid losing past investments in the testing of the mix design, as well as due to the consideration that past mix design performance may be needed or requested for a future project.

However, it is on account of the rapidly growing number of mix designs that concrete producers find it increasingly difficult to confirm whether an existing mix design will meet specific requirements of a future customer. This is especially true if there occurs a change in a material that is required in a large portion of the mix designs within the mix catalog. The very act of re-evaluating a myriad of existing mix designs means that a lot of time would be required to sift through a collection of mix designs to confirm that a specific desired performance would be attained by a given mix design within the collection. The growing number of mix designs impedes the ability as well as thwarts the determination of a quality control group to manage the mix design catalog. In other words, the large number of mix designs leads to a limited ability to check performance through physical testing as the effort is spread out over the many mix designs. This dilutes the quality of information for any one mix design which leads to a higher overdesign as required by standards such as ACI 318-14. Thus, the present inventors believe that the very proliferation of mix designs is in itself a vexing cost magnifier for concrete producers.

Although there are methods for creating new mix designs including the ACI method of mix design (ACI 211.1-91), methods developed by Ken Day (Concrete Mix Design, Quality Control and Specification), methods developed by Francois de Larrard (Concrete Mixture Proportioning), and Per Andersen ((See e.g., U.S. Pat. No. 7,386,368 wherein the use of a "K factor" is disclosed for generating new mix designs), no methods exist at present for managing the various mix designs that a concrete producer has accumulated in its mix design catalog over time, based on real time rheology monitoring processes.

Accordingly, the present inventors believe that the concrete industry needs a novel and inventive way to manage efficiently and effectively the mix design catalog of a concrete producer.

SUMMARY OF THE INVENTION

In addressing the problem of ever-expanding mix design catalogs of concrete producers, the present invention facilitates the ability of a concrete producer to organize, to manage, and to select a mix design from within a highly populated concrete mix design catalog, and, ultimately, to reduce the number of mix designs required to be considered for meeting given project requirements, thus concentrating information per given mix design, eventually leading to less overdesign.

The invention provides both a process and system that may be implemented, using monitoring devices and components that are commercially available in the concrete industry, in accordance with the teachings as shall be particularly described herein.

An exemplary process of the invention for managing a plurality of mix designs within the mix design catalog of a concrete producer, comprises: collecting slump curve data obtained during monitoring of individual concrete loads made from a plurality of various mix designs, wherein each mix design is identified by a different identification code regardless of whether the mix components are different or are identical; clustering (or collating) slump curve data having same movement characteristics into at least two slump curve data clusters; associating each mix design within the slump curve data cluster to an assigned strength value; and selecting a mix design to produce, to display, or both to produce and to display, from among the two or more individual mix designs within the same slump curve data cluster, the selection being based on same assigned strength value and on at least one selection factor chosen from cost, performance, physical aspect, quality, or combination thereof.

An exemplary system of the invention for managing a plurality of mix designs within the mix design catalog of a concrete producer, comprises: a plurality of concrete ready-mix delivery trucks each having a computer processor unit (CPU) communicative with a first sensor or sensors for measuring the energy associating with rotating a concrete mix load within a rotating mixer drum (e.g., such as a hydraulic pressure sensors, a strain or stress gauge type sensors, etc.) and communicative with a second sensor for measuring the rotational speed of the mixer drum (e.g., an accelerometer), wherein the CPUs are programed to store into CPU-accessible memory a plurality of slump data curves obtained during in-transit delivery monitoring of individual concrete loads made from a plurality of various mix designs (as identified by individual mix design number or identification code, regardless of whether its mix components are identical or different); and a computer processor unit which is programmed (the computer processor is chip, circuit, machine, hardware, etc., either on truck, remote location, e.g., so-called cloud-based system which is not necessarily on truck or at control center location): (a) to collate (e.g., cluster) the slump curve data that were obtained during and from in-transit delivery monitoring of individual concrete loads made from a plurality of various mix designs (as identified by individual mix design number or identification code, regardless of whether its mix components are identical or different) according to assigned strength values; and (b) to select, to display, or both to select and to display a preferred mix design chosen from the collation of a plurality of slump curve data at a given assigned strength value, based on at least one selection factor (e.g., cost of mix components or overall mix, cement type, aggregate type, admixture type, w/c, and numerous other possible selection factors).

In exemplary embodiments of the invention, the selection factor may be chosen from cost, performance, physical property or characteristic, or other considerations. Examples of selection factors can include (a) material cost of the mix design; (b) material cost of any of the mix components; (c) number of previous deliveries; (d) total volume delivered of a particular concrete mix design; (e) number of strength test results available; (f) submittal approval statuses; (g) source of materials used in the concrete mix; (h) a characteristic or property of an aggregate material used in the mix design; (i) a characteristic or property of hydration of cement used in the mix design; (j) a characteristic or property of packing density within the concrete mix; (k) a characteristic or property of the durability or reactive nature of the concrete mix; (l) a characteristic or property of the placement of the concrete mix; (m) chemical admixture used in the concrete mix; (n) air characteristic of the concrete; (o) diameter of hose or pipe used for conveying concrete from delivery truck, mixer, or pump to the actual placement site at the construction location; or (p) a combination of any of the foregoing factors.

At the outset, the concrete producer may assign a strength value to a give concrete mix using any number of available methods. Typically, when a new mix design is produced, using, for example, ACI 211.1-91, conservative estimates for the w/c can be used to achieve a given strength. For example, a 28 day strength of 6000 psi may be achieved with a w/c of 0.41 for a non-air entrained concrete mix, subject to an actual physically produced test mix made to ensure correct properties, such as slump and strength. According to standards such as ACI 318-14, to achieve a design strength (to satisfy the structural requirements of the concrete), one is forced to strive for higher strength averages. This is based on the variability of production and because of this inherent variability (which may be reduced with tighter quality control), the mix design must be overdesigned to ensure that the design strength is met on a statistically acceptable basis. Frequently, in the mix designs, the design strength is designated, and for instances of this invention, can be one way to assign the strength criteria. Other factors may help to assign design strengths, for example, the producer might initially begin by using the standard w/c as an indication of strength value. More sophisticated strength methods exist. The producer might alternatively use the methods of Anderson et al. in U.S. Pat. No. 7,386,368 wherein strength, slump, and cost are estimated by using a "K factor" which involves consideration of the influence of a plant's materials on concrete strength, although the present inventors suspect this process could be overwhelming as material sources change over time.

The present inventors unexpectedly found that mix designs could exist with vastly different mix constituents but that could surprisingly share the same rheology characteristics, and vice-versa, that mix designs with seemingly similar mix constituents could have different movement (e.g., slump) behavior. The present invention provides a process for managing highly populated mix design catalogs that have a high number of superfluous mix designs; and it affords a number of advantages, as described in the following paragraph.

Quality control managers will be able to pare down from hundreds and possibly thousands of mix designs to perhaps twenty or thirty mix designs. This will facilitate quality control, allowing managers to focus on the variation of fewer mix designs, and perhaps to identify more quickly the causes of the variations. Fewer mix designs means that the concrete producer can spend more time per mix design, thus providing for greater volumes of information per mix design and hence accuracy in terms of slump monitoring as well as in strength testing; or, in other words, the producer can thus more rapidly obtain insight into how concrete mixes perform on a more statistically meaningful basis. This can result in avoidance of over-designing a mix (e.g., adding extra cement to ensure strength requirements are met), and allow the producer to optimize a mix design without, for example, spending money on extra cement.

The invention also provides exemplary methods for generating new concrete mix designs based on information obtained from, such as interpolated from, existing an mix design catalog containing information of rheology and strength values, and actually or empirically derived based on existing mix designs. For example, a process for creating a new concrete mix design, comprising: collecting slump curve data obtained during monitoring of individual concrete loads made from a plurality of various concrete mix designs, wherein each concrete mix design corresponds to a different identification code regardless of whether the mix components are different or are identical; clustering slump curve data having same movement characteristics into at least two slump curve data clusters; associating each mix design within the slump curve data cluster to an assigned strength value; inputting a target strength and rheology; interpolating mix design components based on at least two existing mix designs wherein the strength and rheology targets are satisfied; and creating a new mix design to produce, to display, or both to produce and to display, based on the mix design components interpolated from the at least two existing mix designs.

Further advantages and features of the invention are discussed hereinafter.

BRIEF DESCRIPTION OF DRAWINGS

An appreciation of the benefits and features of the invention may be more readily comprehended when the following written description of preferred embodiments is considered in conjunction with the drawings as described in the following paragraphs.

DETAILED DESCRIPTION OF EXEMPLARY EMBODIMENTS

A. Definitions

Figure 1:
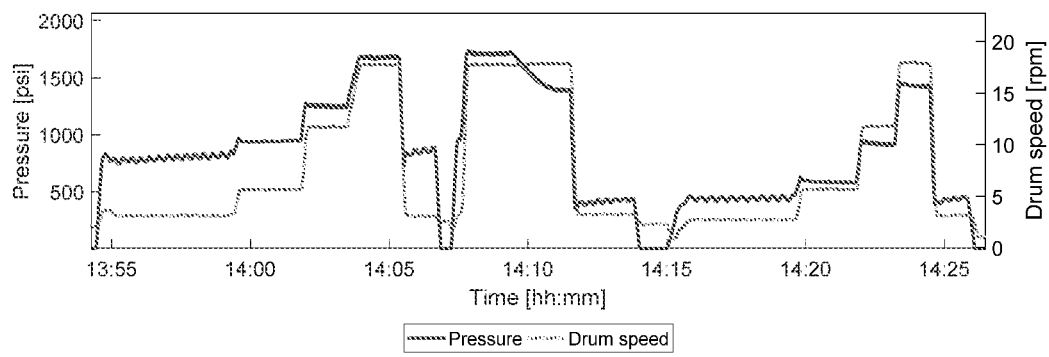
FIG. 1 is graphic illustration of an automated concrete monitoring process wherein the energy (e.g., hydraulic pressure in terms of pounds per square inch as measured along the left vertical axis) associated with rotating a concrete mix load within a rotatable mixer drum is monitored at different drum speeds (e.g., revolutions per minute or "rpm" as indicated on the right vertical axis) over time (as measured in hours:minutes as indicated on the horizontal axis).

The term "concrete" refers to a mixture of cement (which often contains supplementary cementitious materials such as limestone, fly ash, granulated blast furnace slag and other pozzolanic materials) and aggregates (e.g., fine aggregate such as sand, coarse aggregate such as gravel) and optionally one or more chemical admixtures (e.g., plasticizers for increasing workability, set accelerators, set retarders, air entrainers, air detrainers, plastic shrinkage reducing admixtures, corrosion inhibitors (for rebar) for modifying concrete in its plastic or hardened state. Concrete is considered to be hydratable material in that the addition of water into the mixture of cement and aggregates initiates a hardening reaction.

The term "cement" includes hydratable cement such as Portland cement which is produced by pulverizing clinker consisting of hydraulic calcium silicates, aluminates and aluminoferrites, and one or more forms of calcium sulfate (e.g., gypsum) as an interground additive. Typically, Portland cement is combined with one or more supplemental cementitious materials, such as fly ash, granulated blast furnace slag, limestone, natural pozzolans, or mixtures thereof, and provided as a blend, all of which bind aggregates together to make concrete.

The term "aggregate" means and refer to sand and stone particles, typically having average size of 0.5 to 50 mm. Aggregates may also comprise calciferous, siliceous or siliceous limestone minerals. Such aggregates may be of either the "natural" type (e.g., derived from glacial, alluvial, or marine deposits which are typically weathered such that the particles have smooth surfaces) or may be of the "manufactured" type, which are made using mechanical crushers or grinding devices. Coarse aggregate stone particles are typically grouped into various size fractions as described for instance in ASTM C33-16e. As the size fraction used is controlled by various factors, including, but not limited to, the space between reinforcing bars in a proposed construction, aggregate size is often a much considered factor in designing a concrete mix. Aggregates can also mean and refer to lightweight aggregates, such as expanded shale, pumice, sintered fly ash or other low-density fillers.

The terms "concrete mix design," "mix design," and "mixture proportion" refer to the ingredients and proportions of ingredients used for making a given concrete having one or more desired properties, whether in a plastic state, hardened state, or both. A concrete mix is often designed based on various factors, such as, for example, cement type, aggregate type, w/c ratio, chemical admixture, air characteristic, and other factors or ingredients. These and various other "selection factors" will be further discussed hereinafter, once a general discussion of how various concrete mixes from a concrete producer's mix design catalog is monitored for slump curve data.

The term "mix design catalog" refers generally to a collection, compilation, or repository of various mix designs within the control of a concrete producer and which is accessible by a computer-processor. This may refer to one or more electronic files or folders, including storage locations in the cloud or among various computer devices or computer-processor systems, under the control of and subject to access by the concrete producer.

Mix designs are designated by a "mix code" or symbol which is an identifier for the particular proportions of ingredients. A set of identical proportions of ingredients may have different mix codes. Furthermore, a mix code within a given producer's collection of mix codes may refer to different proportions of ingredients. This case arises when the same basic mix design is used at different concrete plants owned or controlled by a single concrete producer. Because each individual concrete plant may source materials from different places (e.g. aggregates from different local quarries), the proportions of ingredients may vary slightly.

The proportions of mix design components (e.g., cement, aggregate, water, optional admixtures) may be expressed as amounts of material per volume of concrete (e.g. 611 pounds of cement per cubic yard of concrete). The proportions may also be expressed as fractions or percentages (e.g. 3 ounces of a superplasticizer admixture per 100 pounds of cement). The concrete components are often described in terms of types: such as cement, supplementary cementitious materials, aggregates (fine, coarse, or both), water, and admixtures. The components may individually be characterized in terms of type or source.

For example, if more than one source of a particular material exists for a producer, the mix design might indicate the particular type (e.g. cement ASTM Type I versus cement ASTM Type III, or ASTM C33 #57 stone versus ASTM C33 #7 stone), or source (e.g. coarse aggregate that is dug from a river bed versus coarse aggregate that is crushed from a quarry).

Additional information may be included in the mix design, along with the proportions of ingredients, such as, for example, target performance values. These performance values may be a design strength (e.g. strength at 28 days), a target slump or slump range, a target air content or air range, a durability target or range (e.g. shrinkage, creep, etc.), etc.

The term "assigned strength" refers to a strength value associated with a particular mix design. The concrete producer typically assigns a number corresponding to compressive strength value (usually in units of pounds per inch or PSI) such as obtained from empirical testing of cylinder samples made in accordance with standards such as ACI 211.1-91 and ACI 318-14. Whereas ACI 211.1-91 designates a design strength (i.e. strength to satisfy structural requirements), a required average strength is designated by ACI 318-14, where this value takes into account both the design strength and variability of the produced the mix design. Thus, the required average strength includes an overdesign from the design strength to ensure that the design strength is met on a statistically acceptable basis. The assigned strength value or number may be chosen to be the design strength or the required average strength. Alternatively, the concrete producer may assign a strength number based on w/c, cement content, packing fraction or other factors.

The term "slump curve data" as used herein will refer to data required to predict slump or other rheological parameter such as yield stress, viscosity, thixotropy, etc., based on sensor readings monitoring mixing vessels such as a mixer drum on a concrete truck or stationary mixer in a precast concrete plant. Different applications may require different rheology considerations (e.g., lower viscosity for pumping through hoses). Examples of sensor readings include mixer drum rotation, energy required to rotate the drum, force on an internal probe within the mixer among others. The slump curve data allows prediction of the slump based on the movement of the concrete within the mixer, and hence provides a description of the movement of the concrete within the mixer.

The term "slump" as used herein will refer to the property of concrete workability, such as determined using the conventional vertical drop measurement of concrete using a standard truncated cone (see e.g., ASTM C143-15a); but this could also include "slump flow" whereby workability is determined using horizontal spread measurement of concrete when released from cone (see e.g., ASTM C1611-14). The term "slump characteristic" may be used also to refer to either or both of these rheological properties and to emphasize that the present invention is not limited necessarily to either slump or slump flow measurements or monitoring, but can comprehend related rheology values such as yield stress as well. The term "slump" is used for sake of convenience herein in referring to concrete rheology and concrete management/monitoring systems.

B. Concrete (Slump) Monitoring Systems

The "energy" (E) associated with rotating concrete within the mixer drum can be monitored using hydraulic pressures sensors whose output may be correlated with slump, slump flow, yield stress, viscosity, or other rheology value (See e.g., U.S. Pat. No. 8,118,473 of Compton et al., U.S. Pat. No. 8,020,431 of Cooley et al., and U.S. Pat. No. 8,989,905 of Sostaric et al., owned by Verifi LLC, a business unit of GCP Applied Technologies Inc. of Cambridge, Mass., USA.

U.S. Pat. No. 8,727,604 of Compton et al. (also owned by Verifi, LLC) disclosed that sensors for monitoring hydraulic pressure associated with rotating the mixer drum could be used with rotational speed sensors to qualify a calculation of the current slump based on the hydraulic pressure required to rotate the mixer drum, such that an accurate history of slump behavior at various drum speeds could be recorded into computer-processor-accessible memory and used at a later time. Preferably, such sensors are used on both the charge and discharge ports of the hydraulic system that controls the mixer drum motor.

The energy associated with rotating the concrete in a mixer drum can also be monitored using force or stress probes within the concrete mixer drum. In these cases, the force or stress of concrete on the probe is measured as the probe rotates through concrete during drum rotation and is correlated with slump of the concrete (See e.g., U.S. Pat. Nos. 8,858,061 and 9,199,391).

Hence, hydraulic pressure sensors, force or stress or strain gauges, and the like, may be used in combination with rotational speed sensors (e.g., accelerometers as mentioned in U.S. Pat. No. 8,727,604 of Compton et al.; US Pat. Publ. No. 2015/0142362 of Jordan et al.; U.S. Pat. No. 9,199,391 of Beaupre et al., and US Pat. Publ. No. 2015/0355160 of Berman, etc.) to provide output values that can be correlated with slump, slump flow, yield stress, viscosity, and/or other rheology values for monitoring or predicting the behavior or rheological state of a concrete mix in a rotatable mixer drum.

Automated concrete slump management (monitoring) systems for managing slump or other rheological properties are commercially available, for example, from Verifi LLC, 62 Whittemore Avenue, Cambridge, Mass., USA, which has disclosed various automated concrete monitoring methods and systems in the patent literature, such as U.S. Pat. Nos. 8,020,431; 8,118,473; 8,311,678; 8,491,717; 8,727,604; 8,746,954; 8,764,273; 8,818,561; 8,989,905; 9,466,803; 9,550,312; PCT/US2015/025054 (Publ. No. WO 2015/160610 A1); and PCT/US2014/065709 (Publ. No. WO2015073825 A1).

Alternatively, the slump monitoring system may be based on use of a force sensor which is mounted within the drum, as taught for example in U.S. Pat. Nos. 8,848,061 and 9,625,891 of Berman (Sensocrete Inc., which is owned by GCP Applied Technologies Inc.), U.S. Pat. No. 9,199,391 of Denis Beaupre et al. (Command Alkon Inc.), or US Publication No. 2009/0171595 and WO 2007/060272 of Benegas.

Thus, while energy/speed/slump ("EVS") relations wherein the energy (E), drum speed (V), and slump (S) can be established using any of a variety of sensor types, the inventors also like to consider the relationship between correlated energy (whether measured as a pressure, force, or stress reading) changes as the concrete mixer drum speed changes, such that the correlations between E, V, and S are not linear in nature. Accordingly, the present inventors have taken to describing the EVS relationship in terms of "slump curves" since a two-dimensional plot of energy (e.g., hydraulic pressure) associated with rotating the concrete at different drum speeds (V) appears as a curve or curvilinear shape rather than a straight line with respect to slump (or slump flow, viscosity, etc.).

Furthermore, these EVS relationships between energy/speed/slump vary for different concrete mixes. In the PCT Publication No. WO 2017/099711, entitled "Wide Speed Range Concrete Monitoring Calibration," Tregger and Roberts et al. disclosed a method for calibrating automated monitoring systems by examining the EVS relationships across different mix designs as well as across a wide range of concrete mixer drum rotational speeds. However, the benefits of the teachings in WO 2017/099771 gave rise to a more refined level of rheological data that could not otherwise be obtained using mere sensors to measure a given rheological property such as slump, as these benefits are not restricted to measurement of just slump value alone.

An appreciation of the present invention will be enhanced by an explanation of the evolutionary advancements in concrete (slump) monitoring systems. This begins with discussion of how energy required for rotating concrete in a mixer drum was initially correlated with slump to obtain a "slump curve." This progresses to a discussion of refinements in the conceptualization of slump curves and slump "ladder" testing. These earlier problems and their resolution gave rise to the surprising, unpredictable discoveries that underpin the instant invention.

C. Wide Speed Range Jumps: Building Slump Ladders Using Curve Data

Originally, it was assumed there was a simple relationship between energy associated with the movement of concrete in a mixer drum and the slump of the mix at a given drum rotation speed. To understand this relationship, the maker of the monitoring system had to perform what was termed a "ladder" process or test. The slump ladder process required the maker to adjust slump incrementally from one and nine inches or more through water or admixture additions; and to measure slump manually at each increment using the conventional slump cone method (e.g. ASTM C143-15a or ASTM C1611-14) to enable sensor data to be correlated with measured slump values. As sensor data was analyzed at different drum speeds, the relationship between pressure/speed/slump could be used for predicting slump for the entire fleet. This relationship was referred to as a "slump curve."

As illustrated in FIG. 1, the average drum speed and hydraulic pressures are recorded during a ladder test on each of three "step ups" in drum speed (as shown at times of 13:55, 14:00 and 14:02 in FIG. 1). At approximately 14:07, a sample was removed from the drum, and pressure goes to "0". Thereafter, slump was adjusted as seen by the pressure dropping (at 14:10) so that the process of changing drum speed could be repeated to generate the slump curve data.

However, it was subsequently realized that a large number of relationships were required in order for the system to be able to be able to monitor accurately all drum rotation speeds across a ready-mix producers' mix designs and fleet of delivery truck types. It was realized also that each truck type and truck manufacturer had unique properties that affected the generation of slump curve data, which such factors often caused three times the slump ladder tests to be run for the fleet of a given concrete producer.

Figure 2:
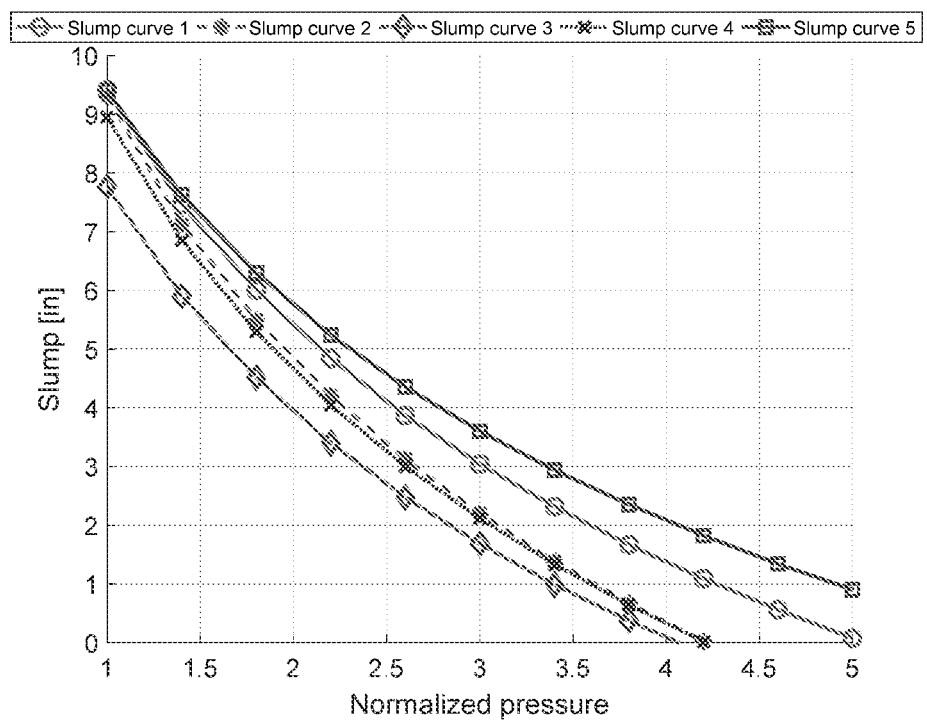
FIG. 2 is a graphic illustration of curves representing energy (e.g., hydraulic pressure) and slump data values corresponding to five different concrete mix designs, as monitored at a constant drum rotation speed.

FIG. 2 shows the results of multiple slump curves derived from multiple ladder testing. As can be seen in FIG. 2, a slump of 4 inches at a constant drum rotation speed was seen to correspond with a range of hydraulic pressures from 1500 to 2000 pounds per inch (psi). This means that a reading of 1500 psi could correspond to a slump of 3.5 to 7 inches. These possible correlations were unacceptable for accurate slump measurement purposes; and, thus, multiple slump curves needed to be generated. It was realized that viscosity was critical to generation of slump curve data, and this required the creation of multiple curves for a single concrete producer.

Initial attempts to resolve this complexity included bucketing the concrete mixes into mix categories or families of similar mixes in a prescriptive manner, i.e., by considering similar cement content, w/c, or aggregate packages. As there was no easy way of measuring viscosity of a given mix without additional field testing, the assumption was that mixes having similar constituents would have similar viscosity and slump curves.

Figure 3:
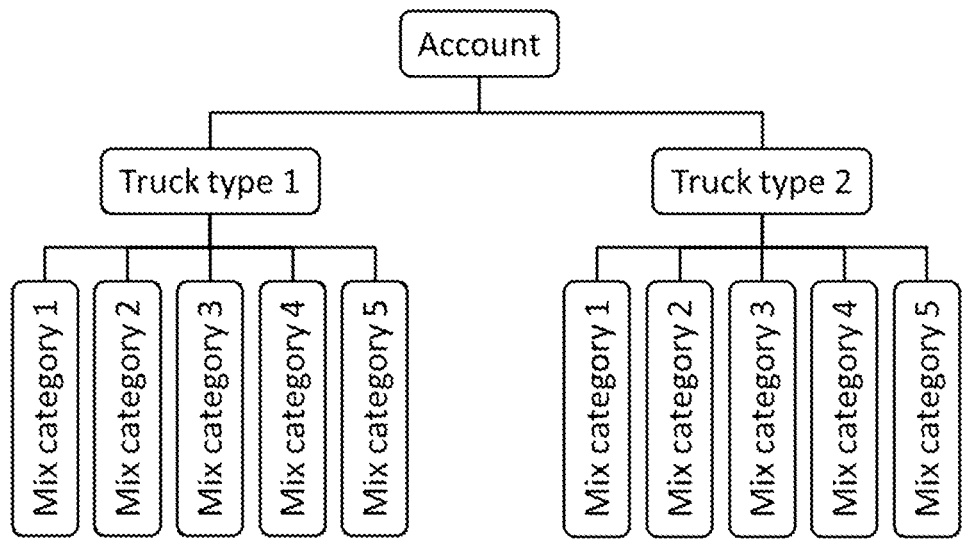
FIG. 3 is a schematic illustration that suggests the multiplicative number of "slump ladder" calibrations that might be required for one ready-mix concrete plant account for which a concrete producer may need to deliver concrete loads made from a number of mix types (i.e. groups of mix designs having e.g. similar water or cement contents) and a number of different mixer truck types.

In other words, the apparent need for ladder testing meant a long and arduous ladder process, one requiring expenditures in terms of concrete purchases and testing time in terms of weeks if not months of establishing slump ladders manually using slump cones. FIG. 3 illustrates the exploding number of slump curves that were necessary, at one point, to be generated for a single concrete producer. Adding to this ladder testing complexity were several difficulties. One difficulty was the fact that the prescriptive grouping method tended to be inaccurate at higher drum speeds, since the effect of viscosity could be surprisingly different within a group of mix designs. This was particularly true at lower w/c and in higher-cement mixes, slump curve behavior would be more pronounced, thus requiring manual slump cone testing for certain mix designs in order for the monitoring system to be accurate. Lastly, the concrete producer's slump curve data was never updated; this became a problem as the component materials changed (without notice) and affected the performance of the concrete.

The beginning of the turn-around for the present inventors started with the realization that manual ladder testing could be replaced by using monitoring calibration techniques involving truck-mounted mixer drum "jump" speed data that was selectively assimilated from previous deliveries. A process and method for calibration of an automated concrete delivery-vehicle based monitoring system was taught by Tregger & Roberts et al. in PCT/US2015/064257 (published as International Publication No. WO 2017/09711 A1), which is incorporated by reference herein. These inventors realized that drum speeds are constantly changing during delivery across a wide range of drum speeds, and that at multiple times the speed changes by more than 4 rpm (hence "jumps") in either direction (in mixing or discharge mode) and that the pressure or force corresponding to drum movement followed suit with those jumps. They also realized that this change took place in less than five seconds and that the actual slump of the concrete remained the same across those five seconds. By measuring pressure and speed before and after a speed jump, and assuming slump was the same before and after the speed jump, then the relationship between Slump1 as a Function of (Speed1, Pressure1) and Slump2 as a Function of (Speed2, Pressure2), where Slump1=Slump2, would mean that there is a functional relationship, F(Speed1, Pressure1)=F(Speed2, Pressure2), such that if one knew the slump at either Slump1 or Slump2, then slump ladders could be replaced by using passively collected sensor data. In order to determine either of the slumps, one of two methods were suggested. Both methods relied on relationships between slump and pressure that could be applied to nearly all mix designs within a concrete producer's catalog. The first method took advantage that at low speed (e.g. below 3 rpm), one or two relationships between pressure and slump could be assumed to cover an entire concrete producer's mix designs. The second method involved one or two relationships between the slump and the slope and intercept from a drum rotation speed and pressure plot to cover the entire concrete producer's mix designs.

Figure 4:
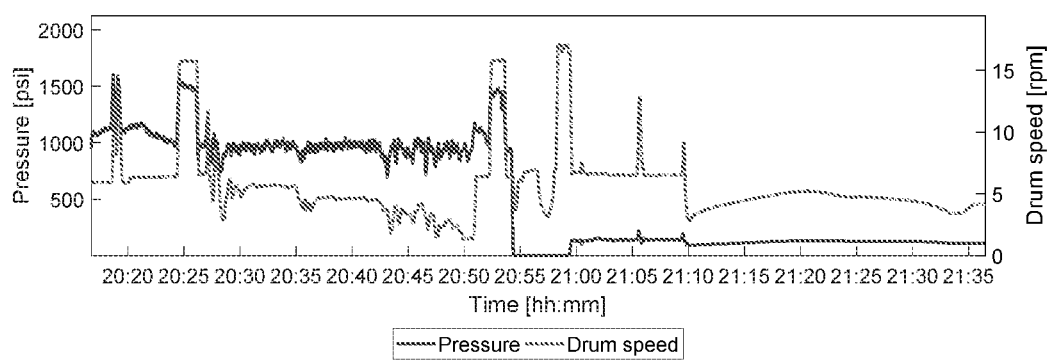
FIG. 4 is a graphic illustration of pressure/drum speed as monitored over time, wherein the solid line illustrates hydraulic pressure (psi) and the dotted line illustrates drum speed (rpm), and wherein elapsed time is designated along the horizontal axis.

FIG. 4 illustrates a typical concrete delivery from the "perspective" of pressure and drum speed sensors from which three jump speed data can be used for establishing slump curves that replace manually obtained slump ladders. In FIG. 4, the solid blue line (associated with the left vertical axis) illustrates the hydraulic pressure measurement while the dotted orange line (associated with the right vertical axis) illustrates the drum speed, both measured against time (horizontal axis). After loading, the truck drum speed jumps (at approximately 20:25) to perform high speed mixing (16-17 rpm). The drum speed then jumps back down and after which, the truck travels to the job site using in-transit drum speeds (2-4 rpm). Upon arrival at the site (at approximately 20:52), and just before discharge, the drum speed increases to high agitation speeds (~15-17 rpm), and subsequently decreases before discharge. This demonstrates how jump speed data points can be collected for both high and low speed/pressures for the same concrete slump.

D. Pairing Clustered Slump Curve Data with Assigned Strength

While the above illustrates the process for starting to build the relationship between pressure, drum speed and slump, this did not necessarily connect to strength. To start, by compiling large sets of slump curve data obtained from thousands of concrete deliveries, involving different concrete mix and delivery truck types, and examining at different constant speed ranges, the present inventors discovered that certain different concrete mix designs may demonstrate the same slump curve behavior. In other words, the inventors discovered that the slump curve data for different mix designs (i.e., having different mix codes) coincided or "clustered" about the same data curve shape or lines; the slump curve data is grouped based on performance (rheology), not a prescriptive measure (i.e. cement content, w/c, etc.). Again, the term "cluster" or "clustered" or other variant thereof, as used in this document, means and refers to the act of collating or compiling mix designs (as identified by a mix code) having the same concrete movement behavior. Hence, the word cluster has both a passive and active sense. These clustered mix designs can then be sorted according to an assigned strength value.

Figure 5:
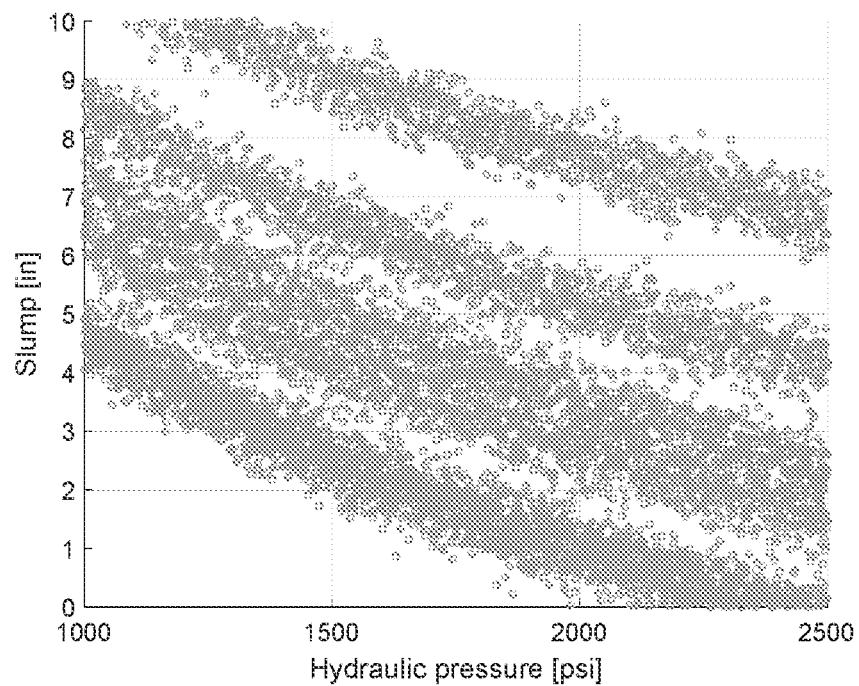
FIG. 5 is a graphic illustration of numerous curves corresponding to a number of concrete mixes of different mix designs that were monitored for slump (vertical axis) and hydraulic pressure (horizontal axis) at one drum speed.
Figure 6:
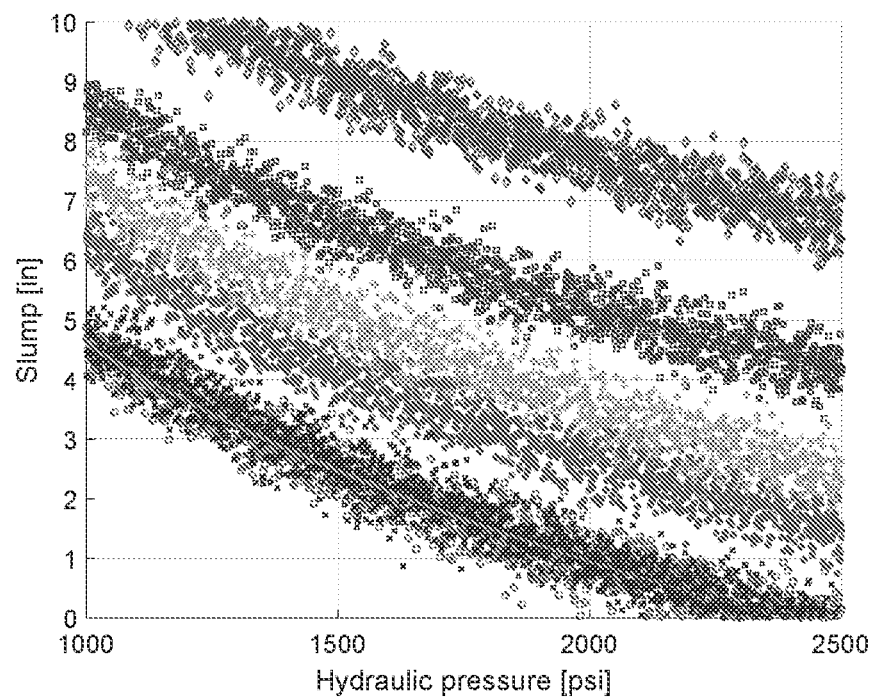
FIG. 6 is a graphic illustration of data curves generated by measuring slump (vertical axis) against hydraulic pressure (horizontal axis) for six different mix designs at one drum speed, wherein the two different mix designs at the bottom of the graph are seen to define the same slump/pressure curve behavior, and thus are deemed to move in the same way and thus can be collated or compiled as one data curve "cluster" for purposes of reducing the number of concrete mix designs, which may be done using one or more selection factors, as taught according to the present invention.

FIG. 5 graphically illustrates hydraulic pressure and slump relationships at one drum speed and at first appears to present four distinct curves, while FIG. 6 graphically illustrates that the data set, using different colors, corresponds in reality to six different concrete mix designs (i.e., mix designs having different codes and possibly different or similar or same recipes). The bottom-most curve is comprised of purple and green marks (x and o); the green line shown through this bottom curve represents the equation generated by that data. This means that the same equation or data curve can be used to predict slump for both mix designs. It also means that the concretes made from the two mix designs move in the same manner (i.e. performance based clustering versus prescriptive).

The present inventors surprisingly discovered that two or more mix designs could have the same curve, and, hence, what they term a "cluster" of slump curve data that essentially appear as a single curve phenomenon. From the coincidence of the two mix designs illustrated in FIG. 6, the present inventors realized that a clustering algorithm can be used that takes into account truck type and mix design to cluster mixes into a slump curve if the mix designs are determined to move in the same manner. The mathematical field of cluster analysis is a large and active field including over one-hundred published clustering algorithms. Thus, numerous mathematical methods can be employed to obtain slump curves that are similar to each other. Examples of clustering algorithms are centroid models, such as the k-means algorithm; distribution models such as the expectation-maximization algorithm; density models such as the DBSCAN algorithm; neural models, such as the self-organizing map algorithm, and even soft clustering models, such as the fuzzy clustering models, which determines how objects belong to a cluster by their "degree" of fit. As an example, two slump curve data sets can be clustered if the resulting slump curve determined from each of the data sets predicts slump values sufficiently close to each other (e.g. the predictions are within ½ inch from each other).

The present invention is predicated upon the ability to "cluster" slump curve data, i.e., when two or more (and preferably a plurality) of concrete mix designs are found to move similarly, or, in other words, to possess the same energy (e.g., pressure)/speed/slump relationship. As shown in FIG. 6, the two individual mix designs (i.e., having different mix codes) cluster along the same curve. One may see evidence of numerous cluster instances within the mix design catalog of a concrete producer wherein mix designs having different mix codes have the same rheological fingerprint. For example, a mix design catalog containing 1000 mix codes can be reduced by cluster analysis to 20 characteristic slump data curves. Surprisingly, many designs that do not have the same components or recipe can share the same slump curve and hence can be found within the same cluster of curve data points (e.g., as may be visually appreciated when the data is displayed on a graph).

This ability to classify how concrete moves allows the present inventors to line up that classification with another characterization, namely, the strength value which has been assigned by the concrete producer to the concrete mix design (hereinafter the "assigned strength"). The present inventors believe this will enable concrete producers to reduce the size of the mix catalog, to create a preferred mix list, and to enhance quality control. If concrete mixes are found to move in the same manner and have the same strength, there is no reason to have multiple mix designs. The fewer the mix count, the greater, then, would be the volume of slump curve data generated for the particular mix design, and hence the volume of strength test results (e.g., cylinder test, cube test); and this would provide a greater amount of quality control or accuracy in the slump curve predictions, for example, that could be made by the monitoring system processor unit.

Figure 7:
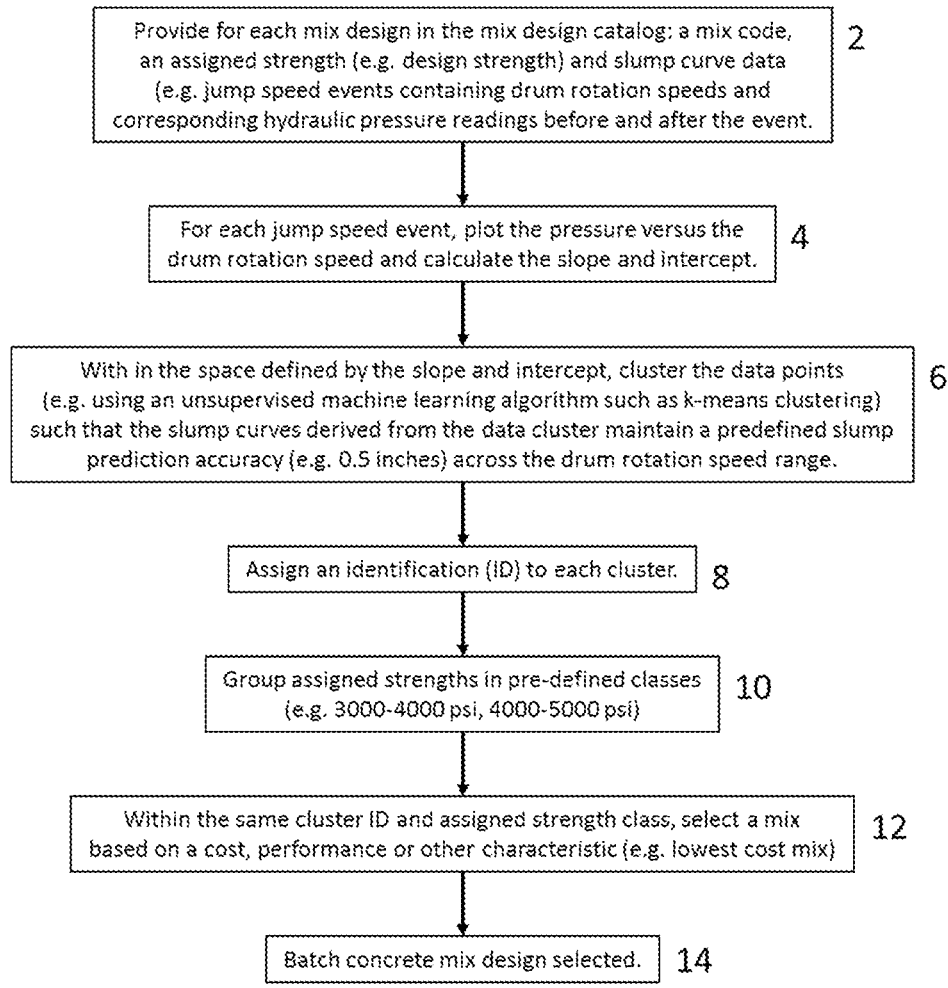
FIG. 7 is a three dimensional histogram wherein 608 total mix designs are mapped according to the number of mix design (indicated along the left vertical axis) belonging to a slump curve cluster (as assigned along the left horizontal axis) and having an assigned strength value (as indicated along the rightmost horizontal axis).

FIG. 7 is a flow chart showing an exemplary process of the present invention. In block 2, a mix design catalog (or a portion, e.g. all residential mixes), is provided that comprises mix designs with a mix code; assigned strengths (e.g. design strengths as determined using ACI 211.4-91 and ACI 318-14); and slump curve data. The slump curve data can be any data used to predict the rheology (i.e. slump) based on the movement detected in the rotating concrete mixer drum. For example, the slump curve data can comprise jump speed events that include the drum rotation speed and corresponding hydraulic pressure readings before and after the event.

In block 4, the slump curve data is prepared for the clustering analysis. For example, with the jump speed data, each jump speed event can be plotted on an x-y plot where the drum rotation speed is plotted on the x-axis and the hydraulic pressure is plotted on the y-axis. For each jump speed event, a line can be drawn through the two points (representing the drum rotation speed and pressure before and after the jump speed), and the slope and intercept can be calculated.

Once these values are calculated, they can be plotted in the slope-intercept space, where the intercept is plotted on the x-axis and the slope is plotted on the y-axis (or vice versa), as is shown in block 6. With this space being defined and filled in with the data, a clustering algorithm can be used to determine clusters within the space. The clustering algorithm can be based upon any of a number of different clustering methods. For example, an unsupervised machine learning algorithm can be used, such as a k-means algorithm (see e.g. Hartigan, J. A.; Wong, M. A. (1979). "Algorithm AS 136: A K-Means Clustering Algorithm". Journal of the Royal Statistical Society. Series C (Applied Statistics). 28 (1): 100-108). After clusters are formed, slump curve relationships can be created for each cluster, and subsequently, the prediction accuracy of each slump curve relationship can be determined. If the accuracy is not sufficient (above a pre-defined accuracy, e.g. 90% of the prediction are with 0.5 inches of the actual slump), the cluster analysis may be refined, for example, to have more finely-divided clusters).

Alternatively, the jump speed events can be plotted on an x-y-z plot where, for example, the drum rotation speed is plotted on the x-axis, the hydraulic pressure is plotted on the y-axis and the slump is plotted on the z-axis. Cluster analysis can then be performed in this "EVS" space to determine slump curve data clusters.

In block 8, once the slump curve clusters have been sufficiently discerned or identified, an identification code or nametag can be assigned to the cluster to facilitate subsequent grouping.

In block 10, the assigned strengths are grouped into pre-defined classes, for example, strengths between 3001 and 4000 psi are put into one class; strengths between 4001 and 5000 psi are put into another class. More preferably, smaller subdivisions can be used, and from a practical perspective, the classes are assigned by the minimum of the range, not the average. This imparts a conservative outlook on the data.

In block 12, a mix design can be chosen within the same slump curve cluster ID and assigned strength class, based on a cost, performance or other characteristic, for example lowest cost. This process can be achieved in several different ways. First, using a fixed selection characteristic (or group of selection characteristics), all mix design groups with the same slump curve cluster and strength class can be reduced to the minimal number of mix designs that still include the given selection characteristic. For example, within the same slump curve cluster and strength class, only the lowest cost mix may be retained for selection to batch, when a mix design requiring the given slump curve cluster rheology and strength class is needed. As another example, the mixes with the highest volume of deliveries may be kept for both an air-entrained version and a non-air-entrained version. The mix designs that are not retained in these two examples can, for example, be excluded from further consideration, archived, or deleted from the mix design catalog. Alternatively, the associated data (slump curve data, strength data, or other data) can be merged with the retained mix design(s). Regardless of the fate of the non-retained mix designs, the retained mix designs, with their future use will accumulate quality control data in order to all better control.

In block 14, the selected mix design is batched.

Figure 8:
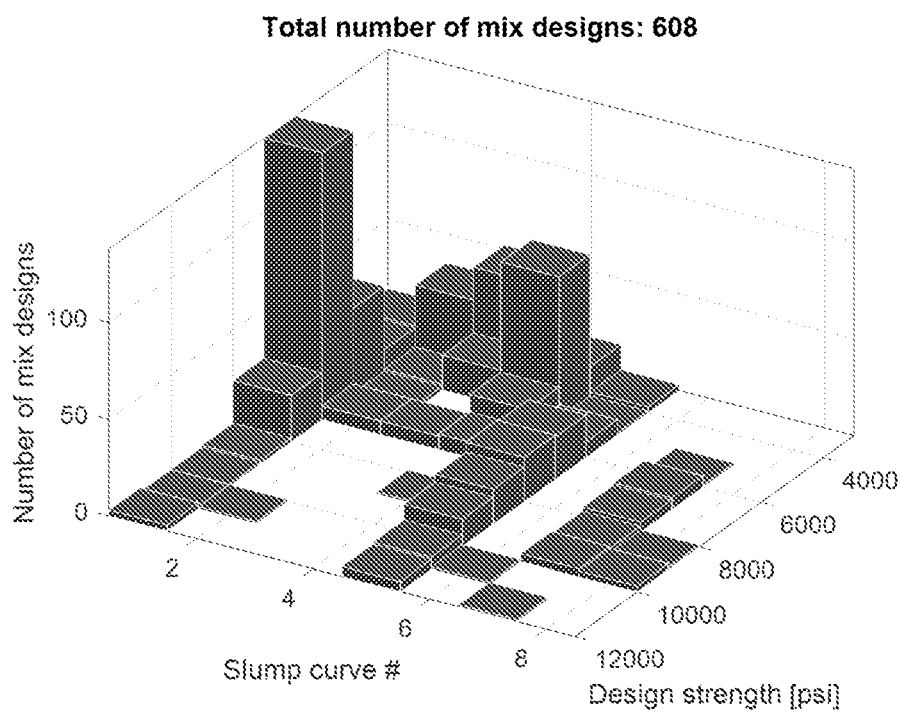
FIG. 8 is a two dimensional chart derived from the three-dimensional histogram of FIG. 7 wherein the 608 total mix designs can be reduced to 37 different total mix designs having the same slump curve behavior (same cluster) at the assigned strength values.

FIG. 8 is a two-dimensional histogram in which 608 concrete mix designs (i.e., 608 different codes) were monitored. Nine different slump curves were discerned among these mix designs for various assigned strength values in the range of 4000 to 12000 psi. The tallest peak, indicating over 100 different mix designs (codes) can be readily seen for slump curve #1 at assigned strength of 7000 psi, and this visually represents a very data-dense slump curve.

Figure 9:
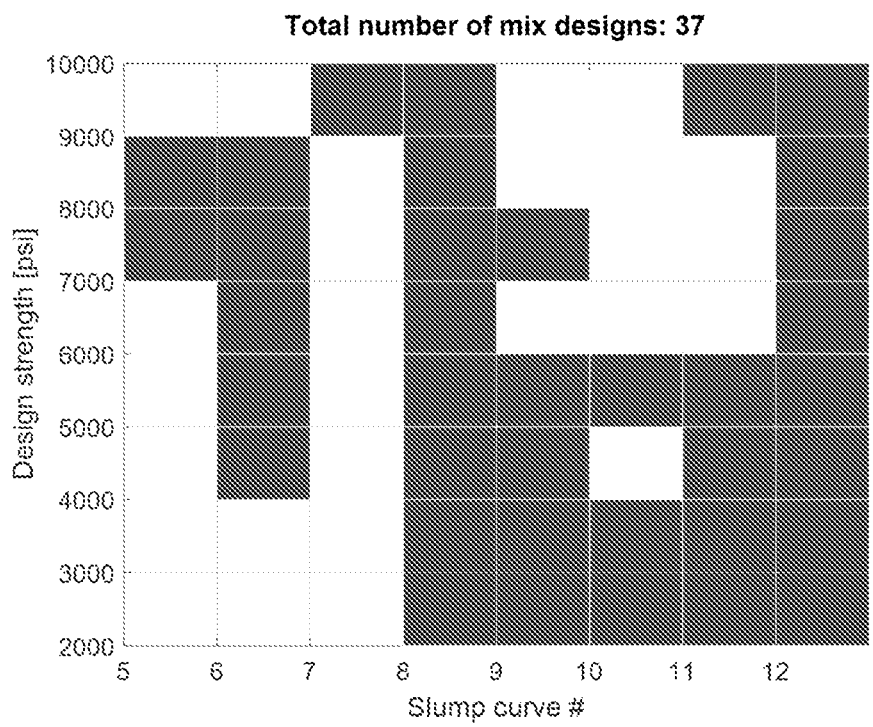
FIG. 9 is a flow chart illustrating various steps within an exemplary process of the present invention.

FIG. 9 is a two-dimensional representation of the histogram of FIG. 7, which indicates that 608 concrete mix designs represent in actuality only 37 different slump curve-strength groups.

As a further advantage of the present invention, new mixes can be tailored to a given application with much higher confidence. Typically, lab tests are performed to validate a design. However, this method may not represent the actual performance as mixing in a small lab mixer does not represent actual mixing experienced in a mixer truck. However, by interpolating between existing mix designs with their associated data (i.e. strength and rheology), mix designs with precise strength and rheology characteristics (beyond a simple slump value) can be developed. Moreover, the amount of associated data garners realistic validation compared to lab tests. Such data can be extremely useful as supporting data for submittals for a given job.

In a first example embodiment, the present invention provides a process for managing a plurality of mix designs within the mix design catalog of a concrete producer, comprising: collecting slump curve data obtained during monitoring of individual concrete loads made from a plurality of various mix designs, wherein each mix design is identified by a different identification code regardless of whether the mix components are different or are identical; clustering slump curve data having same movement characteristics into at least two slump curve data clusters; associating each mix design within the slump curve data cluster to an assigned strength value; and selecting a mix design to produce, to display, or both to produce and to display, from among the two or more individual mix designs within the same slump curve data cluster, the selection being based on same assigned strength value and on at least one selection factor chosen from cost, performance, physical aspect, quality, or combination thereof.

In a second exemplary embodiment, which may be based on the first example embodiment, the invention provides a process wherein, in selecting the mix design, the at least one selection factor is chosen from (a) material cost of the mix design; (b) material cost of any of the mix components; (c) number of previous deliveries; (d) total volume delivered of a particular concrete mix design; (e) number of strength test results available; (f) submittal approval statuses; (g) source of materials used in the concrete mix; (h) a characteristic or property of an aggregate material used in the mix design (e.g., mineralogical nature of the aggregate, shape or size of aggregate such as maximum particle size, pacing fraction, etc.); (i) a characteristic or property of hydration of cement used in the mix design (e.g., w/c, initial set time, final set time, etc.); (j) a characteristic or property of packing density within the concrete mix; (k) a characteristic or property of the durability or reactive nature of the concrete mix (e.g., chloride permeability, alkali-silica reaction susceptibility); (l) a characteristic or property of the placement of the concrete mix; (m) chemical admixture used in the concrete mix (e.g., admixture type, nature of high range water reducer effect, accelerators, retarders, effect of admixture combinations, etc.); (n) air characteristic of the concrete (e.g., air content, air distribution, air spacing factor, etc.); (o) diameter of hose or pipe used for conveying concrete from delivery truck, mixer, or pump to the actual placement site at the construction location; or (p) a combination of any of the foregoing factors.

In a third exemplary embodiment, which is as described above with respect to any of the first through second example embodiments above, the invention provides a process wherein the cluster comprises slump curve data sets associated with different mix designs whereby the slump predictions from the slump prediction relationships derived from each individual slump curve data are within a predefined tolerance (e.g. +/−0.5 inch slump).

In a fourth exemplary embodiment, which is as described above with respect to any of the first through third example embodiments above, the invention provides a process wherein, in collecting slump curve data obtained during monitoring of individual concrete loads made from a plurality of various mix designs, the slump curve data are derived from jump speed data wherein slump, drum rotation speed, and force associated with rotating the concrete mix in a rotating mixer drum are obtained before and after jumps in drum speed, wherein the jump in drum speed is at least three (and more preferably at least four) drum revolutions per minute difference. These factors (e.g., slump, drum rotation speed, and force associated with rotating the concrete mix in a rotating mixer drum) can be saved in a computer-accessible database as grouped relationships. They can be plotted graphically (and thus are described herein in terms of "slump curve data") and displayed in any number of ways. The slump curve data can be defined in terms of force (e.g., hydraulic pressure sensor readings) as a function of drum speed (e.g., rotations per minute at a first drum speed and at a second drum speed which was suddenly changed by at least 3 or 4 RPM compared to the first drum speed). The data comprising the y-intercepts (i.e., the pressure value when speed is extrapolated to zero) and slope (of the pressure values at the two drum speed values) may be subjected to cluster analysis to discern mix designs having common rheological behavior (such as may be suggested by a cloud of dots plotted on a graph which suggest a common trend or singular common grouping—or, in other words, where the dots appear to coincide).

In a fifth exemplary embodiment, which is as described above with respect to any of the first through fourth example embodiments above, the invention provides a process wherein, in collecting slump curve data obtained during monitoring of individual concrete loads made from a plurality of various mix designs, the slump data curves are established using sensors for measuring force associated with rotating concrete mixes in a rotating mixer drum, said force sensors being chosen from hydraulic pressure sensor, stress or strain gauge device located within the rotating mixer drum, or both.

In a sixth exemplary embodiment, which is as described above with respect to any of the first through fifth example embodiments above, the invention provides a process wherein, in collecting slump curve data obtained during monitoring of individual concrete loads made from a plurality of various mix designs, the slump data curves are established using hydraulic pressure sensors comprising a first sensor for measuring hydraulic pressure when the mixer drum is rotating in the charge direction, and a second sensor for measuring hydraulic pressure when the mixer drum is rotating in the discharge direction.

In a seventh exemplary embodiment, which is as described above with respect to any of the first through sixth example embodiments above, the invention provides a process wherein, in collecting slump curve data obtained during monitoring of individual concrete loads made from a plurality of various mix designs, the slump data curves are established using a stress or strain gauge device located inside the mixer drum.

In an eighth exemplary embodiment, which is as described above with respect to any of the first through seventh example embodiments above, the invention provides a process wherein, in collecting slump curve data obtained during in-transit delivery monitoring of individual concrete loads made from a plurality of various mix designs, the slump data curves are established using a drum speed sensor that comprises an accelerometer, a gyroscope, or combination thereof.

In a ninth exemplary embodiment, which is as described above with respect to any of the first through eighth example embodiments above, the invention provides a process wherein, in the step of clustering curve data having same movement characteristics according to assigned strength value, at least two (more preferably at least three, and most preferably at least ten) different mix designs (which are identified as different by having different codes but have the same mix components) are used to make concrete mix loads from which slump curve data is obtained to define the same slump curve and hence define a slump curve data cluster.

In a tenth exemplary embodiment, which is as described above with respect to any of the first through ninth example embodiments above, the invention provides a process wherein the assigned strength values are based on physical strength, modulus of elasticity, water content, cement content, maturity testing, or combination thereof.

In an eleventh exemplary embodiment, which is as described above with respect to any of the first through tenth example embodiments above, the invention provides a process wherein, in collecting slump curve data obtained during in-transit delivery monitoring of individual concrete loads made from a plurality of various mix designs, slump curve data establish at least three (and more preferably at least five) different slump curve data clusters; and are correlated with at least three (and, more preferably, at least five) assigned strength values.

In a twelfth exemplary embodiment, which is as described above with respect to any of the first through eleventh example embodiments above, the invention provides a process wherein a concrete mix design is selected from a cluster of slump curve data for an assigned strength (e.g., value or number) by operation of computer processor, and a concrete mix is generated. In a further example of this particular aspect, the computer processor has been programmed to select the concrete mix design and to instruct that a concrete mix be made (e.g., by sending signal to the batching computer at the batch plant) according to the selected mix design. Preferably, the computer processor is programmed to initiate this function without further inputs from a human operator or manager.

In a thirteenth exemplary embodiment, which is as described above with respect to any of the first through twelfth example embodiments above, the invention provides a process wherein a histogram (See e.g., FIG. 8) or chart (See e.g., FIG. 9) is generated to depict graphically, on a monitor screen or other visual display, the slump curve data clusters for each assigned strength value.

In a fourteenth exemplary embodiment, which is as described above with respect to any of the first through thirteenth example embodiments above, the invention provides a process wherein the histogram or chart displayed on a monitor screen is a GUI (graphical user interface) allowing a user to click to view a list of mix codes for a given cluster of slump curve data.

In a fifteenth exemplary embodiment, which is as described above with respect to any of the first through fourteenth example embodiments above, the invention provides a process wherein, after selecting a mix design to produce, to display, or both to produce and to display, from among the two or more individual mix designs within the same slump curve data cluster, at least one mix design is removed from the same slump curve data cluster. For example, one or more of the selection factors identified within the second exemplary aspect discussed above may be used for inactivating or removing from the producer's catalog those mix designs which exceed a given cost threshold, which employ a given cement or aggregate material, or which meet any other selection criteria based on the selection factors.

In a sixteenth exemplary embodiment, the invention provides system for managing a plurality of mix designs within the mix design catalog of a concrete producer, comprising: a plurality of concrete ready-mix delivery trucks each having a computer processor unit (CPU) communicative with a first sensor or sensors for measuring the energy associating with rotating a concrete mix load within a rotating mixer drum (e.g., such as a hydraulic pressure sensors, a strain or stress gauge type sensors, etc.) and communicative with a second sensor for measuring the rotational speed of the mixer drum (e.g., an accelerometer), wherein the CPUs are programed to store into CPU-accessible memory a plurality of slump curve data obtained during in-transit delivery monitoring of individual concrete loads made from a plurality of various mix designs (as identified by individual mix design number or identification code, regardless of whether its mix components are identical or different); and a computer processor unit which is programmed (the computer processor is chip, circuit, machine, hardware, etc., either on truck, remote location, e.g., so-called cloud-based system which is not necessarily on truck or at control center location): (a) to collate (e.g., cluster) the slump curve data that were obtained during and from in-transit delivery monitoring of individual concrete loads made from a plurality of various mix designs (as identified by individual mix design number or identification code, regardless of whether its mix components are identical or different) according to assigned strength values; and (b) to select, to display, or both to select and to display a preferred mix design chosen from the collation of a plurality of slump curve data at a given assigned strength value, based on at least one selection factor (e.g., cost of mix components or overall mix, cement type, aggregate type, admixture type, w/c, and numerous other possible selection factors).

In a seventeenth exemplary embodiment, which is as described above with respect to the sixteenth example embodiment described above, the invention provides a system wherein, in selecting the mix design, the at least one selection factor is chosen from (a) material cost of the mix design; (b) material cost of any of the mix components; (c) number of previous deliveries; (d) total volume delivered of a particular concrete mix design; (e) number of strength test results available; (f) submittal approval statuses; (g) source of materials used in the concrete mix; (h) a characteristic or property of an aggregate material used in the mix design (e.g., mineralogical nature of the aggregate, shape or size of aggregate such as maximum particle size, pacing fraction, etc.); (i) a characteristic or property of hydration of cement used in the mix design (e.g., w/c, initial set time, final set time, etc.); (j) a characteristic or property of packing density within the concrete mix; (k) a characteristic or property of the durability or reactive nature of the concrete mix (e.g., chloride permeability, alkali-silica reaction susceptibility); (l) a characteristic or property of the placement of the concrete mix; (m) chemical admixture used in the concrete mix (e.g., admixture type, nature of high range water reducer effect, accelerators, retarders, effect of admixture combinations, etc.); (n) air characteristic of the concrete (e.g., air content, air distribution, air spacing factor, etc.); (o) diameter of hose or pipe used for conveying concrete from delivery truck, mixer, or pump to the actual placement site at the construction location; or (p) a combination of any of the foregoing factors.

In an eighteenth exemplary embodiment A process for creating a new concrete mix design, comprising: collecting slump curve data obtained during monitoring of individual concrete loads made from a plurality of various concrete mix designs, wherein each concrete mix design corresponds to a different identification code regardless of whether the mix components are different or are identical; clustering slump curve data having same movement characteristics into at least two slump curve data clusters; associating each mix design within the slump curve data cluster to an assigned strength value; inputting a target strength and rheology; interpolating mix design components based on at least two existing mix designs wherein the strength and rheology targets are satisfied; and creating a new mix design to produce, to display, or both to produce and to display, based on the mix design components interpolated from the at least two existing mix designs. This eighteenth example embodiment may be based upon, or incorporate any of the feature described above with respect to the first through seventeenth example embodiments.

While the invention is described herein using a limited number of embodiments, these specific embodiments are not intended to limit the scope of the invention as otherwise described and claimed herein. Modifications and variations from the described embodiments exist. More specifically, the following examples are given as a specific illustration of embodiments of the claimed invention. It should be understood that the invention is not limited to the specific details set forth in the examples. All parts and percentages in the examples, as well as in the remainder of the specification, are by percentage dry weight unless otherwise specified.

Example 1

As an example of the surprising advantages and benefits of the present invention, the present inventors considered the mix design catalog of an actual concrete producer which contained 608 mix designs (as identified by 608 different mix codes). This was actually a subset of the entire mix catalog because it was limited to a given region, which used the same aggregate source. The mix designs were filtered to include only coarse aggregates having a nominal size of one inch. This filtering process can occur, alternatively, after applying the inventive steps of FIG. 7, when choosing at least one mix to represent a given strength and rheology characteristic. When organized by strength and rheology (slump relationship), the histogram in FIG. 8 shows the numerous mix designs with the same properties. After applying the inventive steps of FIG. 7, the histogram indicates that mix designs in the strength and rheology "buckets" or groupings shown in FIG. 9 constitute 37 in total, and this represents a reduction of 96% in terms of the previous total number of mix designs in the collection.

Example 2

As a second example, the same reduced set of mix designs in the first example can be used to determine a new mix design with a given set of criteria such as a strength class and a rheology class.

Figure 10:
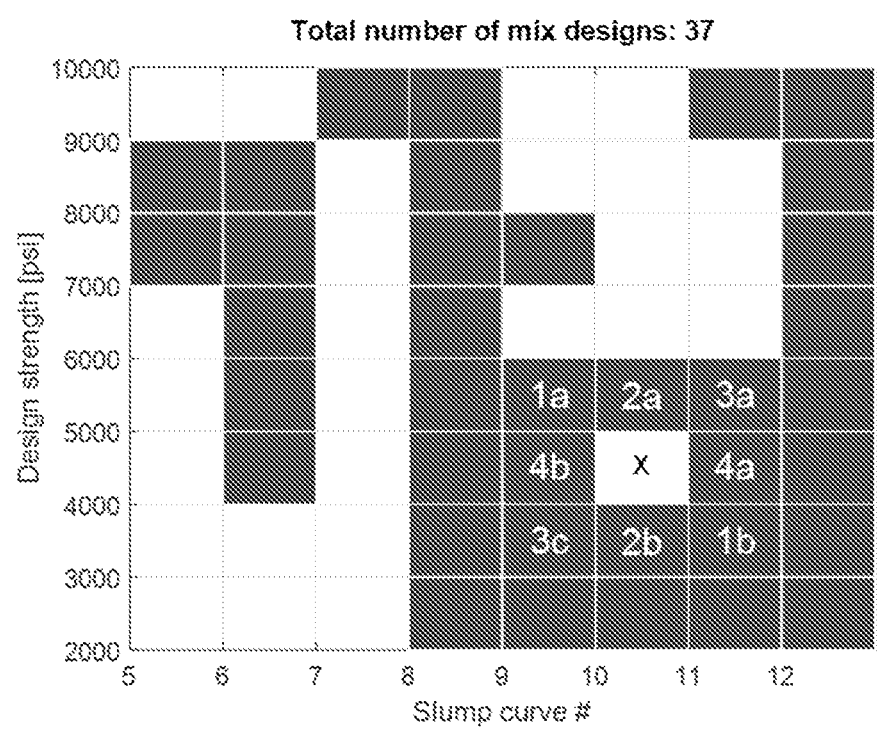
FIG. 10 is a two dimensional chart which illustrates an exemplary method of the invention for interpolating a new concrete mix design based upon information from an existing concrete mix catalog.

As illustrated in a hypothetical example which is illustrated using the two dimensional chart in FIG. 10 (which is based upon FIG. 8 discussed above), a concrete producer may want to supply a mix design with a slump curve and design strength in the space indicated by the bucket or square designated as "x" in FIG. 10. Because no mix design currently exists (for certain combinations of strength and rheology classes), the producer will need to design a new mix.

To design a new mix (for bucket "x"), the producer may draw upon production data corresponding to adjacent buckets, such as using values interpolated based on adjacent buckets. For example, an interpolation can be made by averaging mix proportions belonging to buckets $1a$ and $1b$. Accordingly, a new mix for "x" can be designed.

Further exemplary methods of the invention may include averaging of other adjacent mix designs, such as averaging bucket values of buckets of, e.g., $2a+2b$; $3a+3b$; $4a+4b$, or combinations thereof. The values interpolated for a given bucket "x" can involve values from adjacent spaces in the existing mix design catalog, such as from buckets that may be horizontally, vertically, or diagonally adjacent (in the two dimensional chart representation provided in FIG. 10).

A major advantage of this exemplary method is that actual production data is used to create the new mix design as opposed to lab tests that may not reflect what will actually be produced.

Thus, the invention provides an exemplary process for creating a new concrete mix design, comprising: collecting slump curve data obtained during monitoring of individual concrete loads made from a plurality of various concrete mix designs, wherein each concrete mix design corresponds to a different identification code regardless of whether the mix components are different or are identical; clustering slump curve data having same movement characteristics into at least two slump curve data clusters; associating each mix design within the slump curve data cluster to an assigned strength value; inputting a target strength and rheology; interpolating mix design components based on at least two existing mix designs wherein the strength and rheology targets are satisfied; and creating a new mix design to produce, to display, or both to produce and to display, based on the mix design components interpolated from the at least two existing mix designs.

The present invention is described herein using a limited number of illustrative embodiments not intended to limit the scope of the invention.

It is claimed:

1. A process for managing a plurality of mix designs within a mix design catalog of a concrete producer, comprising:

collecting slump curve data obtained during monitoring of individual concrete loads made from a plurality of various mix designs, wherein each mix design is identified by a different identification code regardless of whether the mix components are different or are identical;

wherein in collecting slump curve data obtained during monitoring of individual concrete loads made from a plurality of various mix designs, slump data curves are established using sensors for measuring force associated with rotating concrete mixes in a rotating mixer drum, said force sensors being chosen from hydraulic pressure sensor, stress or strain gauge device located in the rotating mixing drum, or both;

clustering slump curve data having same movement characteristics into at least two slump curve data clusters;

associating each mix design within the slump curve data cluster to an assigned strength value;

selecting a mix design to produce, to display, or both to produce and to display, from among the two or more individual mix designs within the same slump curve data cluster, the selection being based on same assigned strength value and on at least one selection factor chosen from cost, performance, physical aspect, quality, or combination thereof; and concentrating performance information in said mix design catalog by merging slump curve data, strength data or other data associated with the mix designs not selected with the selected mix design.

2. The process of claim 1 wherein, in selecting the mix design, the at least one selection factor is chosen from (a) material cost of the mix design; (b) material cost of any of the mix components; (c) number of previous deliveries; (d) total volume delivered of a particular concrete mix design; (e) number of strength test results available; (f) submittal approval statuses; (g) source of materials used in the concrete mix; (h) a characteristic or property of an aggregate material used in the mix design; (i) a characteristic or property of hydration of cement used in the mix design; (j) a characteristic or property of packing density within the concrete mix; (k) a characteristic or property of the durability or reactive nature of the concrete mix; (l) a characteristic or property of the placement of the concrete mix; (m) a chemical admixture used in the concrete mix; (n) an air characteristic of the concrete; (o) a diameter of hose or pipe used for conveying concrete from delivery truck, mixer, or pump to the actual placement site at the construction location; or (p) a combination of any of the foregoing selection factors.

3. The process of claim 1 wherein, the clusters comprise slump curve data sets associated with different mix designs whereby slump predictions from slump prediction relationships derived from each individual slump curve data are within a pre-defined tolerance.

4. The process of claim 1 wherein, in collecting slump curve data obtained during monitoring of individual concrete loads made from a plurality of various mix designs, the slump curve data are derived from jump speed data wherein slump, drum rotation speed, and force associated with rotating the concrete mix in a rotating mixer drum are obtained before and after jumps in drum speed, wherein the jump in drum speed is at least three drum revolutions per minute difference.

5. The process of claim 1 wherein, in collecting slump curve data obtained during monitoring of individual concrete loads made from a plurality of various mix designs, the slump data curves are established using sensors for measuring force associated with rotating concrete mixes in a rotating mixer drum, said force sensors being chosen from hydraulic pressure sensor, stress or strain gauge device located within the rotating mixer drum, or both.

6. The process of claim 1 wherein, in collecting slump curve data obtained during monitoring of individual concrete loads made from a plurality of various mix designs, the slump data curves are established using hydraulic pressure sensors comprising a first sensor for measuring hydraulic pressure when the mixer drum is rotating in the charge direction, and a second sensor for measuring hydraulic pressure when the mixer drum is rotating in the discharge direction.

7. The process of claim 1 wherein, in collecting slump curve data obtained during monitoring of individual concrete loads made from a plurality of various mix designs, the slump data curves are established using a stress or strain gauge device located inside the rotating mixer drum.

8. The process of claim 1 wherein, in collecting slump curve data obtained during in-transit delivery monitoring of individual concrete loads made from a plurality of various mix designs, the slump data curves are established using a drum speed sensor that comprises an accelerometer, a gyroscope, or combination thereof.

9. The process of claim 1 wherein, in the step of clustering slump curve data having same movement characteristics according to assigned strength value, at least two different mix designs are used to make concrete mix loads from which slump curve data is obtained to define a same slump curve and hence define a slump curve data cluster.

10. The process of claim 1 wherein the assigned strength values are based on physical strength, modulus of elasticity, water content, cement content, maturity testing, or combination thereof.

11. The process of claim 1 wherein, in collecting slump curve data obtained during in-transit delivery monitoring of individual concrete loads made from a plurality of various mix designs, the slump curve data establishes at least three different slump curve data clusters; and are correlated with at least three assigned strength values.

12. The process of claim 1 wherein a concrete mix design is selected from a cluster of slump curve data for an assigned strength by operation of computer processor, and a concrete mix is generated.

13. The process of claim 1 wherein a histogram or chart is generated to depict graphically, on a monitor screen or other visual display, slump curve data clusters for each assigned strength value.

14. The process of claim 13 wherein the histogram or chart displayed on a monitor screen is a GUI (graphical user interface) allowing a user to click to view a list of mix codes for a given cluster of slump curve data.

15. The process of claim 1 wherein, after selecting a mix design to produce, to display, or both to produce and to display, from among the two or more individual mix designs within the same slump curve data cluster, at least one mix design is removed from the same slump curve data cluster.

16. A system of the invention for managing a plurality of mix designs within a mix design catalog of a concrete producer, comprising:
 a plurality of concrete ready-mix delivery trucks each having a computer processor unit (CPU) communicative with a first sensor or sensors for measuring the energy associating with rotating a concrete mix load within a rotating mixer drum and communicative with a second sensor for measuring the rotational speed of the mixer drum, wherein the CPUs are programed to store into CPU-accessible memory a plurality of slump curve data obtained during in-transit delivery monitoring of individual concrete loads made from a plurality of various mix designs; and
 a computer processor unit which is programmed
  (a) to collate the slump curve data that were obtained during and from in-transit delivery monitoring of individual concrete loads made from a plurality of various mix designs according to assigned strength values;
  (b) to select, to display, or both to select and to display a preferred mix design chosen from the collation of a plurality of slump curve data at a given assigned strength value, based on at least one selection factor; and
  (c) to concentrate performance information in said mix design catalog by merging slump curve data, strength data or other data associated with the mix designs not selected or displayed with the selected and/or displayed mix design.

17. The system of claim 16 wherein, in selecting the mix design, the at least one selection factor is chosen from (a) material cost of the mix design; (b) material cost of any of the mix components; (c) number of previous deliveries; (d) total volume delivered of a particular concrete mix design; (e) number of strength test results available; (f) submittal approval statuses; (g) source of materials used in the concrete mix; (h) a characteristic or property of an aggregate material used in the mix design; (i) a characteristic or property of hydration of cement used in the mix design; (j) a characteristic or property of packing density within the concrete mix; (k) a characteristic or property of the durability or reactive nature of the concrete mix; (l) a characteristic or property of the placement of the concrete mix; (m) a chemical admixture used in the concrete mix; (n) an air characteristic of the concrete; (o) a diameter of hose or pipe used for conveying concrete from delivery truck, mixer, or pump to the actual placement site at the construction location; or (p) a combination of any of the foregoing selection factors.

18. A process for creating a new concrete mix design, comprising:
 collecting slump curve data obtained during monitoring of individual concrete loads made from a plurality of various concrete mix designs, wherein each concrete mix design corresponds to a different identification code regardless of whether the mix components are different or are identical;
 wherein in collecting slump curve data obtained during monitoring of individual concrete loads made from a plurality of various mix designs, slump data curves are established using sensors for measuring force associated with rotating concrete mixes in a rotating mixer drum, said force sensors being chosen from hydraulic pressure sensor, stress or strain gauge device located in the rotating mixing drum, or both;

clustering slump curve data having same movement characteristics into at least two slump curve data clusters;

associating each mix design within the slump curve data cluster to an assigned strength value;

inputting a target strength and rheology into a computer processor;

interpolating mix design components based on at least two existing mix designs wherein the strength and rheology targets are satisfied; and creating a new mix design to produce, to display, or both to produce and to display, based on the mix design components interpolated from the at least two existing mix designs; and concentrating performance information in said mix design catalog by merging slump curve data, strength data or other data associated with the mix designs not selected with the selected mix design.

* * * * *